(12) United States Patent
Sablone et al.

(10) Patent No.: US 12,396,898 B2
(45) Date of Patent: Aug. 26, 2025

(54) METHOD AND APPARATUS FOR PRODUCING ABSORBENT SANITARY ARTICLES AND RELATIVE ABSORBENT SANITARY PRODUCT

(71) Applicant: Fameccanica.Data S.p.A., San Giovanni Teatino (IT)

(72) Inventors: Gabriele Sablone, San Giovanni Teatino (IT); Massimiliano Rossetti, San Giovanni Teatino (IT); Vincenzo Pezzotta, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 946 days.

(21) Appl. No.: 17/335,611

(22) Filed: Jun. 1, 2021

(65) Prior Publication Data

US 2021/0378879 A1 Dec. 9, 2021

(30) Foreign Application Priority Data

Jun. 5, 2020 (IT) .................... 102020000013339

(51) Int. Cl.
*A61F 13/15* (2006.01)
(52) U.S. Cl.
CPC .......................... *A61F 13/15658* (2013.01)

(58) Field of Classification Search
CPC .......... A61F 13/15658; A61F 13/15747; A61F 2013/15926; A61F 13/15804; A61F 13/15; A61F 13/15577; A61F 13/496; A61F 2013/15821; A61F 2013/15861; A61F 2013/15869
See application file for complete search history.

(56) References Cited

U.S. PATENT DOCUMENTS

2004/0107481 A1* 6/2004 Mortell ............. A61F 13/15723
2/400

FOREIGN PATENT DOCUMENTS

| EP | 0460467 A1 | 12/1991 |
| WO | 0047151 A1 | 8/2000 |
| WO | 2016194481 A1 | 12/2016 |

OTHER PUBLICATIONS

Search Report dated Feb. 18, 2021. 7 pages.

* cited by examiner

*Primary Examiner* — Christopher W Raimund
(74) *Attorney, Agent, or Firm* — RMCK Law Group PLC

(57) ABSTRACT

A method and apparatus for producing pant-like absorbent sanitary articles with longitudinal elastic bands without side welds, wherein a length of the elastic bands is different from a length of an absorbent body.

8 Claims, 8 Drawing Sheets

METHOD AND APPARATUS FOR PRODUCING ABSORBENT SANITARY ARTICLES AND RELATIVE ABSORBENT SANITARY PRODUCT

CROSS-REFERENCE TO RELATED APPLICATION

This application claims priority to Italian Patent Application No. 102020000013339 filed Jun. 5, 2020. The disclosure of the above application is incorporated herein by reference in its entirety.

FIELD OF THE INVENTION

The present invention relates to a method and an apparatus for producing absorbent sanitary articles.

The invention was developed with particular regard to producing absorbent sanitary articles that can be worn as pants, such as the so-called training pants.

The present invention relates, in particular, to a method and an apparatus for producing absorbent sanitary articles according to the so-called "Machine Direction" production technique.

DESCRIPTION OF THE PRIOR ART

Pant-like absorbent sanitary articles are normally formed by an absorbent body and two transverse waistbands (a front waistband and a rear waistband) applied to opposite ends of the absorbent body. The waistbands, usually elastic, can be permanently closed or they can be provided with refastenable closure formations.

For producing pant-like absorbent sanitary articles, a production technique called "Cross Direction" is normally used, which consists of forming two continuous and parallel elastic webs, forming the front and rear waistbands, which advance in a machine direction, and attaching the absorbent bodies transversely between the continuous elastic webs. After applying the absorbent bodies, the two continuous elastic webs are superimposed and fixed to each other transversely at regular intervals by means of transverse welds or by refastenable closure formations.

With this production technique, pant-like absorbent sanitary articles are obtained having welds or refastenable closure formations on their sides.

The presence of welds or refastenable closure formations on the sides of the waistbands reduces the wearability of absorbent sanitary articles.

The market increasingly requires apparatuses capable of producing pant-like absorbent sanitary articles without side welds.

The document WO2000/047151 A1 describes a method for producing pant-like absorbent sanitary articles with permanently closed waistbands and without side welds. The method described in this document envisages the formation of a continuous absorbent composite web that advances in a machine direction in the direction of its longitudinal axis. Two continuous elastic bands are overlapped on respective longitudinal side edges of the continuous absorbent composite web. The continuous elastic bands are fixed to the continuous absorbent composite web along oblique junction lines with a V-shape open outwards. The method involves cutting the continuous composite web and the elastic bands along cutting lines in the shape of a double Y, so as to give rise to discrete absorbent sanitary articles each consisting of an absorbent body and two longitudinal elastic bands fixed at opposite ends of the absorbent body along oblique sides.

The solution known from WO2000/047151 provides absorbent sanitary articles wherein the length of each side elastic band is equal to the length of the absorbent body. With this solution it is problematic to make products with different sizes. For example, in absorbent sanitary articles for babies the circumference of the waistband is small in relation to the length of the absorbent body. In contrast, in absorbent sanitary articles for adults the circumference of the waistband is large in relation to the length of the absorbent body.

OBJECT AND SUMMARY OF THE INVENTION

The present invention aims to provide a method and apparatus for producing absorbent sanitary articles that overcome the problems of the prior art.

In particular, the present invention aims to provide a method and an apparatus that allows production of pant-like absorbent sanitary articles without side welds and with every possible size.

According to the present invention, this object is achieved by a method and by an apparatus having the characteristics forming the subject of claims 1 and 6.

According to another aspect, the present invention relates to an absorbent sanitary article.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

It will be appreciated that the various figures may not be represented on the same scale. It will also be appreciated that some elements or components have not been shown to make other elements/components more visible and to simplify the understanding of the figures.

DETAILED DESCRIPTION

Figure 1:
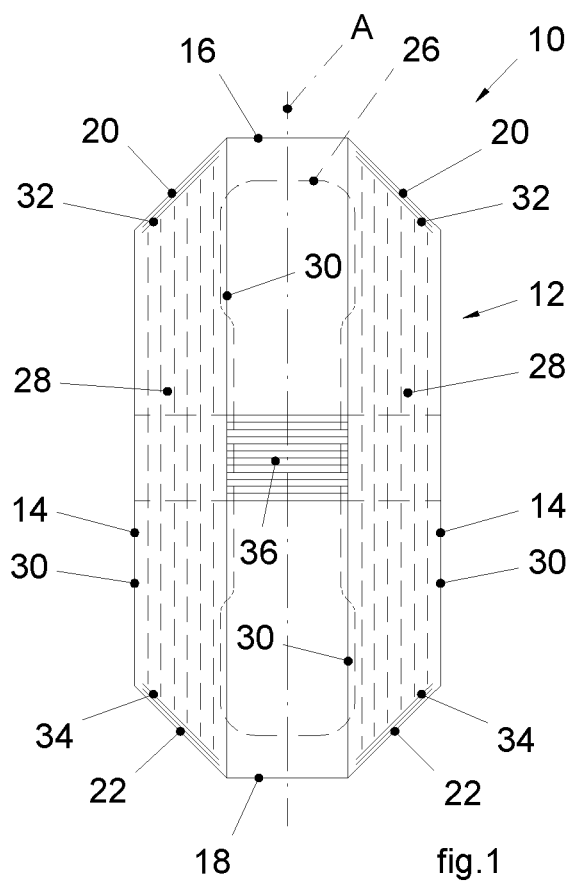
FIG. 1 is a plan view of a first embodiment of an absorbent sanitary article according to the present invention in an extended configuration.
Figure 2:
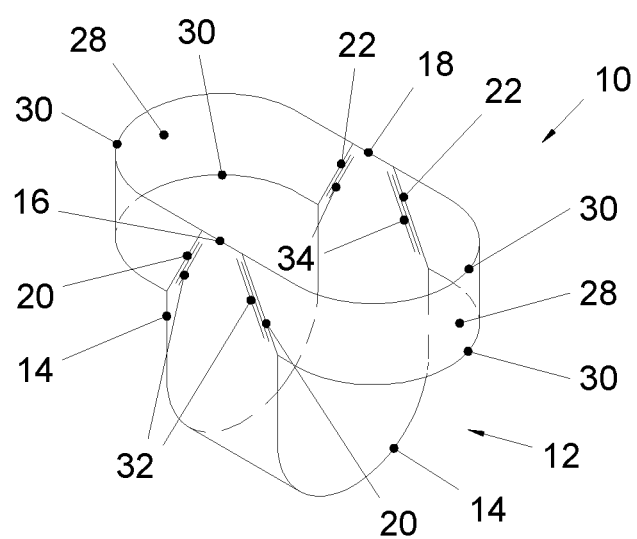
FIG. 2 is a perspective view of the absorbent sanitary article of FIG. 1 in a configuration of use.

With reference to FIGS. 1 and 2, numeral 10 indicates a pant-like absorbent sanitary article according to a first embodiment of the present invention.

The absorbent sanitary article 10 comprises an absorbent body 12 which—in the extended configuration shown in FIG. 1—has an elongated shape along a longitudinal axis A and in the configuration of use shown in FIG. 2 is folded substantially in a U-shape between the legs of the user. The absorbent body 12 has two longitudinal sides 14 that extend along a direction generally parallel to the longitudinal axis A. The longitudinal sides 14 may be straight, as shown by way of example in the figures, or they may be shaped in different ways. The absorbent body 12 comprises a front transverse side 16 and a rear transverse side 18. The absorbent body 12 also has two front oblique sides 20 and two rear oblique sides 22. The two front oblique sides 20 and the two rear oblique sides 22 may be symmetrical with respect to the longitudinal axis A. Each of the oblique sides 20, 22 connects one end of the respective front transverse side 16 or the respective rear transverse side 18 to a corresponding end of the respective longitudinal side 14.

The absorbent body 12 may comprise an absorbent core which may be sandwiched between an inner sheet of liquid-permeable material (topsheet) and an outer sheet of impermeable material (backsheet). Additional absorbent layers may be comprised between the inner sheet and the outer sheet of the absorbent body 12 such as, for example, an Acquisition Diffusion Layer, commonly referred to as ADL. The inner sheet or topsheet of the absorbent body 12 has a surface intended to be facing, during use, towards the user's body. The absorbent body 12 may comprise additional components (not shown) as is customary in the field, such as, for example, elastic elements for the legs (leg cuffs) applied onto the inner sheet and extending parallel to the longitudinal axis A.

The absorbent sanitary article 10 comprises two elastic bands 28 located on opposite sides of the longitudinal axis A. Each of the two elastic bands 28 has two longitudinal sides 30 which, in the extended position of FIG. 1, extend in the direction of the longitudinal axis A. Each of the two elastic bands 28 is fixed to the absorbent body 12 along a front oblique weld 32 parallel to the corresponding front oblique side of the absorbent body 12 and along a rear oblique weld 34 parallel to the corresponding rear oblique side of the absorbent body 12. Each of the two elastic bands is continuous between the front oblique weld 32 and the rear oblique weld 34, and has no welds along the user's sides.

In the extended configuration of FIG. 1, each elastic band 28 extends in the direction of the longitudinal axis A between the front oblique seal 32 and the corresponding rear oblique seal 34, and is superimposed on a corresponding side portion of the absorbent body 12. In a possible embodiment, the outer longitudinal sides 30 of the elastic bands 28 may be aligned with the longitudinal sides 14 of the absorbent body 12.

With reference to FIG. 1, the absorbent body 12 has a loop 36 that extends in a transverse direction between the two longitudinal sides 14. In the configuration of use of FIG. 2, the loop 36 extends and is no longer visible. Taking into account the length of the loop 36, the overall length of the absorbent body in the extended configuration measured between the transverse sides 16 and 18, is greater than the maximum elastic extension of each elastic band 28.

The fact that the absorbent body 12 has a length greater than the maximum elastic extension of each of the elastic bands 28 allows production of pant-like absorbent sanitary articles with sizes typically suitable for children.

Figure 3:
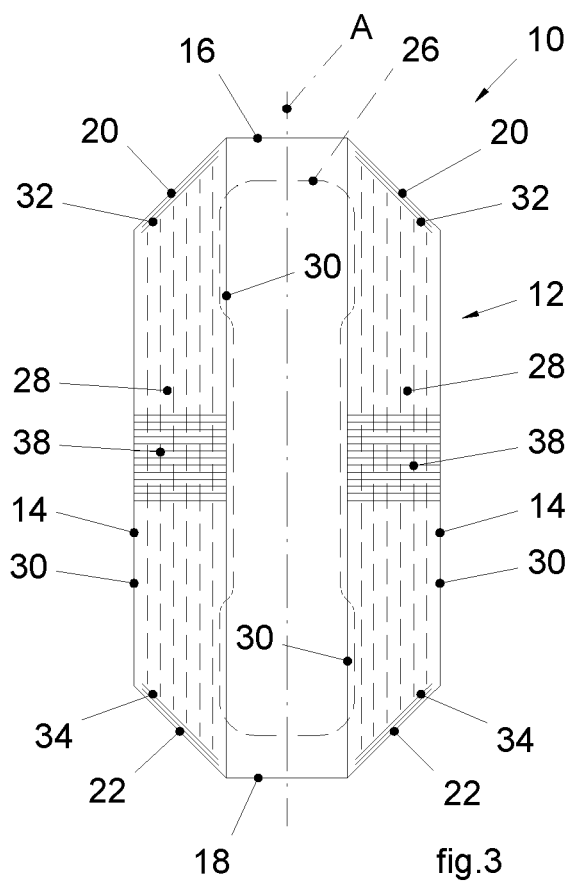
FIG. 3 is a plan view of a second embodiment of an absorbent sanitary article according to the present invention in an extended configuration.
Figure 4:
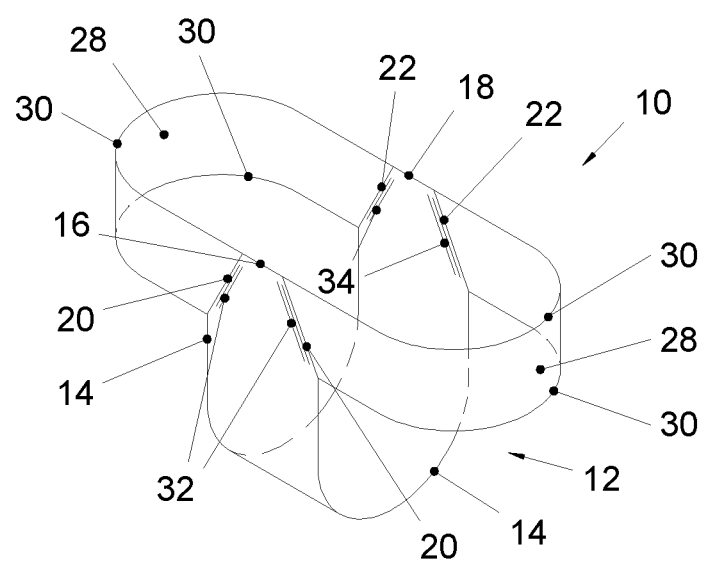
FIG. 4 is a perspective view of the absorbent sanitary article of FIG. 3 in a configuration of use.

FIGS. 3 and 4 show a second embodiment of an absorbent sanitary article 10 according to the present invention. The elements corresponding to those previously described are indicated with the same reference numerals.

In the embodiment of FIGS. 3 and 4, the absorbent sanitary article 10 corresponds to that of FIGS. 1 and 2 with the difference that the absorbent body 12 is devoid of the loop 36. In this embodiment, each of the elastic bands 28 has a respective loop 38 that extends in a transverse direction between two longitudinal sides 30. Taking into account the length of the loops 38, the overall length of each elastic band 28 in an unstretched condition measured between the transverse sides 16, 18, is greater than the length of the absorbent body 12, also measured between the transverse sides 16, 18. The fact that each of the elastic bands 28 in the unstretched condition has a length greater than that of the absorbent body 12 allows production of pant-like absorbent sanitary articles with sizes typically suitable for adults.

Therefore, the fact that the absorbent body 12 has a different length from the unstretched length of each of the elastic bands 28 allows production of pant-like absorbent sanitary articles without side welds and with any size.

In possible embodiments, the loops 36, 38 can be provided both on the absorbent body 12 and on the elastic bands 28.

With reference to FIGS. 5 and 6-13, an embodiment of an apparatus and of a method for producing an absorbent sanitary article 10 of the type shown in FIGS. 1 and 2 will now be described.

Figure 5:
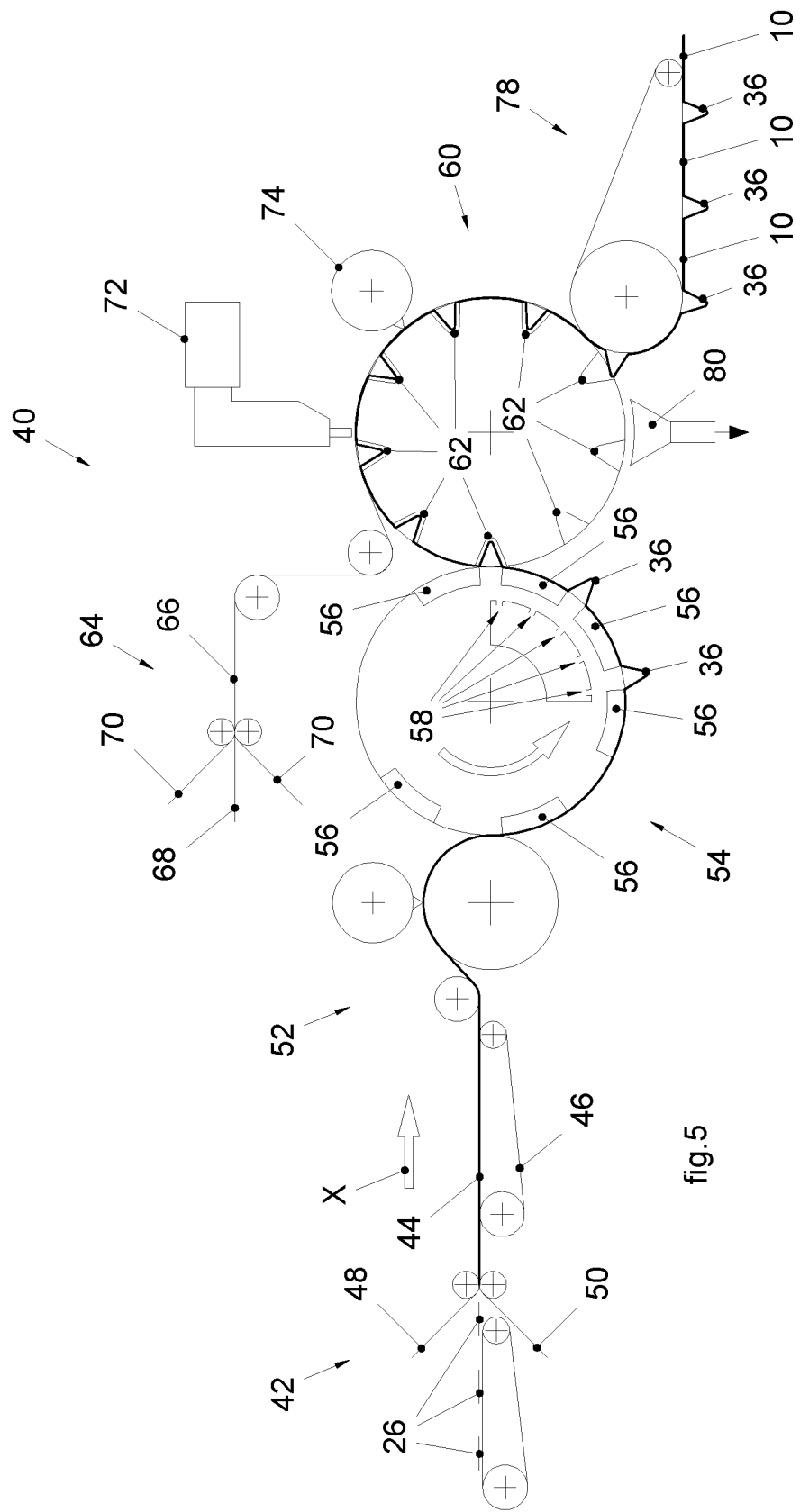
FIG. 5 is a schematic side view of an apparatus configured for producing the absorbent sanitary articles shown in FIGS. 1 and 2, FIGS. 6-13 are schematic plan views showing various steps of a method for producing the absorbent sanitary articles shown in FIGS. 1 and 2.
Figure 6:
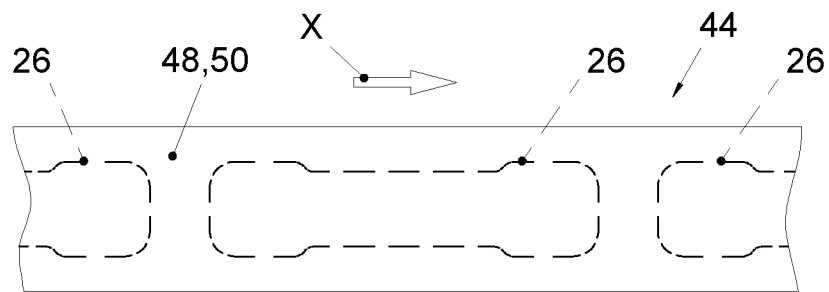
Figure 7:
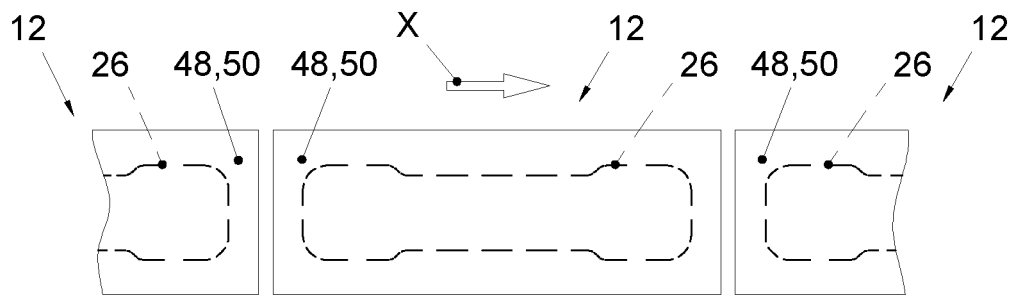

In FIG. 5, an apparatus 40 for producing pant-like absorbent sanitary articles is indicated by 40.

The apparatus 40 comprises a first forming unit 42, configured for forming a continuous absorbent web 44 (FIG. 6) that advances in the machine direction X on a conveyor 46. In the first forming unit 42, a continuous array of absorbent cores 26 is sandwiched between a continuous sheet of topsheets 48 and a continuous sheet of backsheets 50, which are fixed together by conventional techniques in the sector for producing absorbent sanitary articles.

The apparatus 40 comprises a cutting device 52 that transversely cuts the continuous absorbent web 44 to form an array of absorbent bodies 12 (FIG. 7), each of which comprises an absorbent core 26 sandwiched between a topsheet 48 and a backsheet 50.

Figure 8:
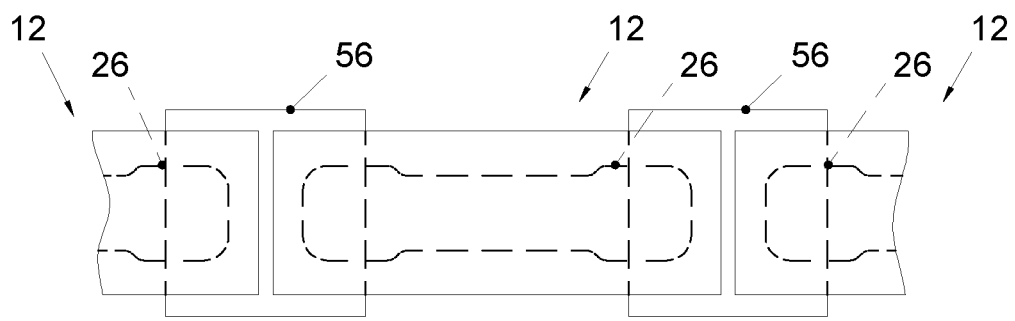
Figure 9:
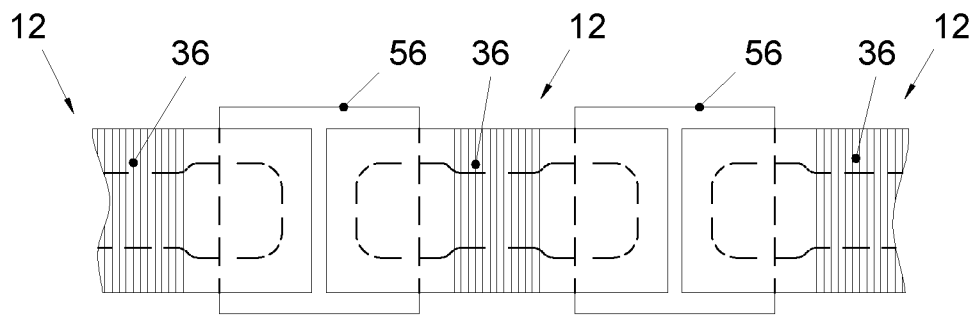

The apparatus 40 comprises a repitching device 54 configured to form transverse loops 36 on respective absorbent bodies 12. The repitching device 54 comprises a plurality of gripping elements 56 rotatable about a common rotation axis with individually controlled speeds. The gripping elements 56 pick up the absorbent bodies 12 in a pick-up station located at the outlet of the cutting device 52 and release them in a release station. The gripping elements 48 may retain the absorbent bodies 12 by suction, according to conventional techniques in the field. Each absorbent body 12 can be held by two gripping elements 56 adjacent to each other. As shown in FIGS. 8 and 9, each gripping element 48 may hold the tail part of a previous absorbent body 12 and the head part of a subsequent absorbent body 12, and the central part of each absorbent body 12 is located in the free space comprised between two gripping elements 56 adjacent to each other. On the way from the pick-up station to the release station, the gripping elements 56 approach each other. FIGS. 8 and 9 schematically shows the position of the gripping elements 56 and of the absorbent bodies 12, respectively, in the pick-up station and in the release station of the repitching device 54. The mutual approach between the gripping elements 56 during movement towards the release station produces the shortening of the absorbent bodies 12 and the formation of loops 36 in the central parts of the absorbent bodies 12 comprised between the gripping elements 56. The repitching device 54 may include nozzles 58 located in the vicinity of the release station and arranged to emit jets of air between the gripping elements 56 so as to push the loops 36 formed on the absorbent bodies 12 outwards.

The apparatus 40 comprises an anvil wheel 60 that receives the absorbent bodies 12 from the repitching device 54. The anvil wheel 60 is provided on its outer surface with recesses 62 that receive respective loops 36 of the absorbent bodies 12. The anvil wheel 60 may retain the absorbent bodies 12 on its surface by suction.

Figure 10:
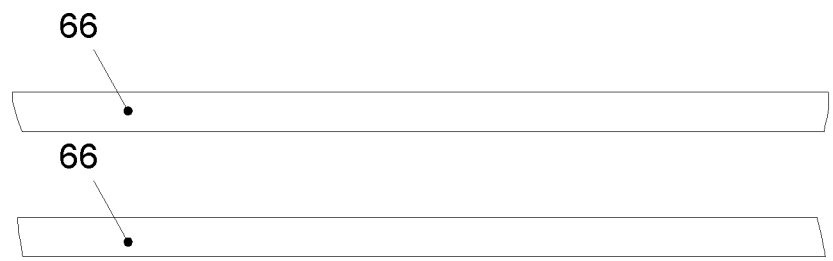
Figure 11:
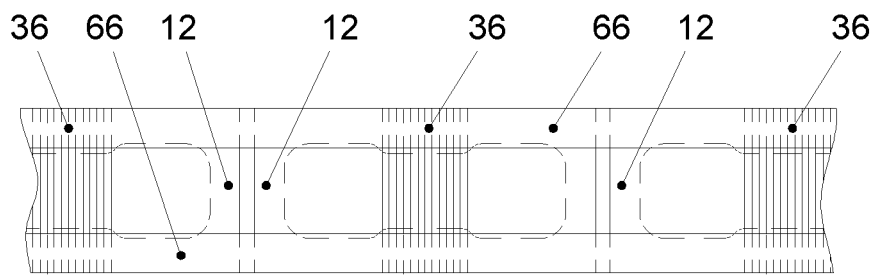

The apparatus 40 comprises a second forming unit 64 configured to form two continuous elastic bands 66 parallel to each other (FIG. 10). The second forming unit 64 may be configured to enclose and attach a plurality of continuous elastic threads 68 between two continuous nonwoven webs 70. The continuous elastic threads 68 may be in a stretched state when enclosed between the two continuous sheets nonwoven webs 70. The continuous elastic bands 66 are fed onto the outer surface of the anvil wheel 60 above the absorbent bodies 12. The continuous elastic bands 66 may be in a stretched state when fed onto the outer surface of the anvil wheel 60. FIG. 11 schematically shows the two continuous elastic bands 60 superimposed on the side portions of the absorbent bodies 12 provided with loops 36.

The apparatus 40 comprises an ultrasonic welding device 72 and a cutting device 74 that cooperate with the anvil wheel 60.

Figure 12:
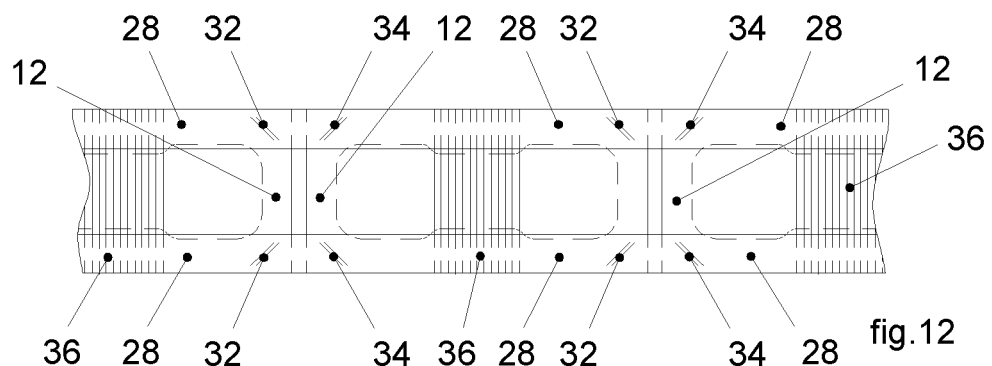

As shown in FIG. 12, the ultrasonic welding device welds the continuous elastic bands 66 to the absorbent bodies 12 along oblique welding lines 32, 34, having a V shape open outwards. The portions of the continuous elastic bands 66 included between the oblique welds 32, 34 form the elastic bands 28 of the finished absorbent sanitary articles 10.

Figure 13:
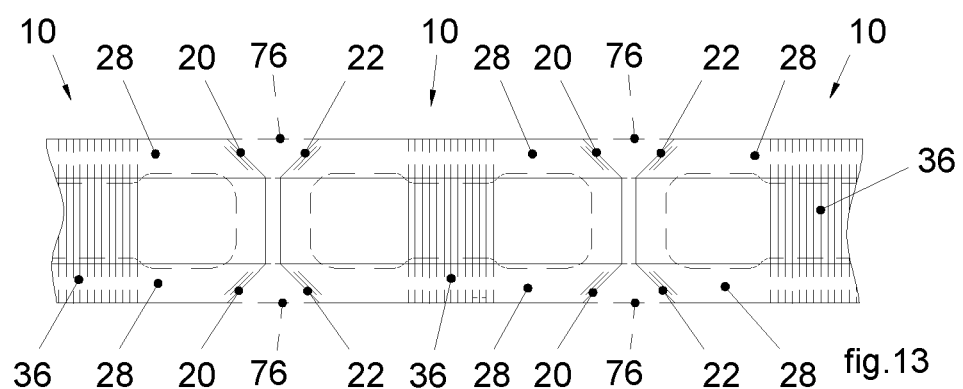

With reference to FIG. 13, the cutting device 74 cuts the continuous elastic bands 66 and the absorbent bodies 12 along oblique cutting lines having a V shape open outwards and adjacent to the welding lines 32, 34. The oblique cutting lines give rise to the oblique sides 20, 22 of the finished absorbent sanitary articles 10. The triangular-shaped portions 76 comprised between the oblique sides 20, 22, indicated by a dashed line in FIG. 13, constitute scraps.

According to a possible embodiment, the oblique welding lines 32, 34 and the corresponding cutting lines, and therefore the oblique front 20 and rear 22 sides of the absorbent article 10, can form an angle between 25° and 65° with the longitudinal axis A, for example, an angle of about 45°, as shown in the figures.

After cutting along the oblique lines 22, 24, finished absorbent sanitary articles 10 are obtained (FIG. 13), which are transferred from the anvil wheel 60 to an outlet conveyor 78. The scraps 76 are evacuated by means of a suction device 80.

With reference to FIGS. 14 and 15-21, an embodiment of an apparatus and of a method for producing an absorbent sanitary article 10 of the type shown in FIGS. 3 and 4 will now be described. The elements corresponding to those previously described are indicated by the same reference numerals.

Figure 14:
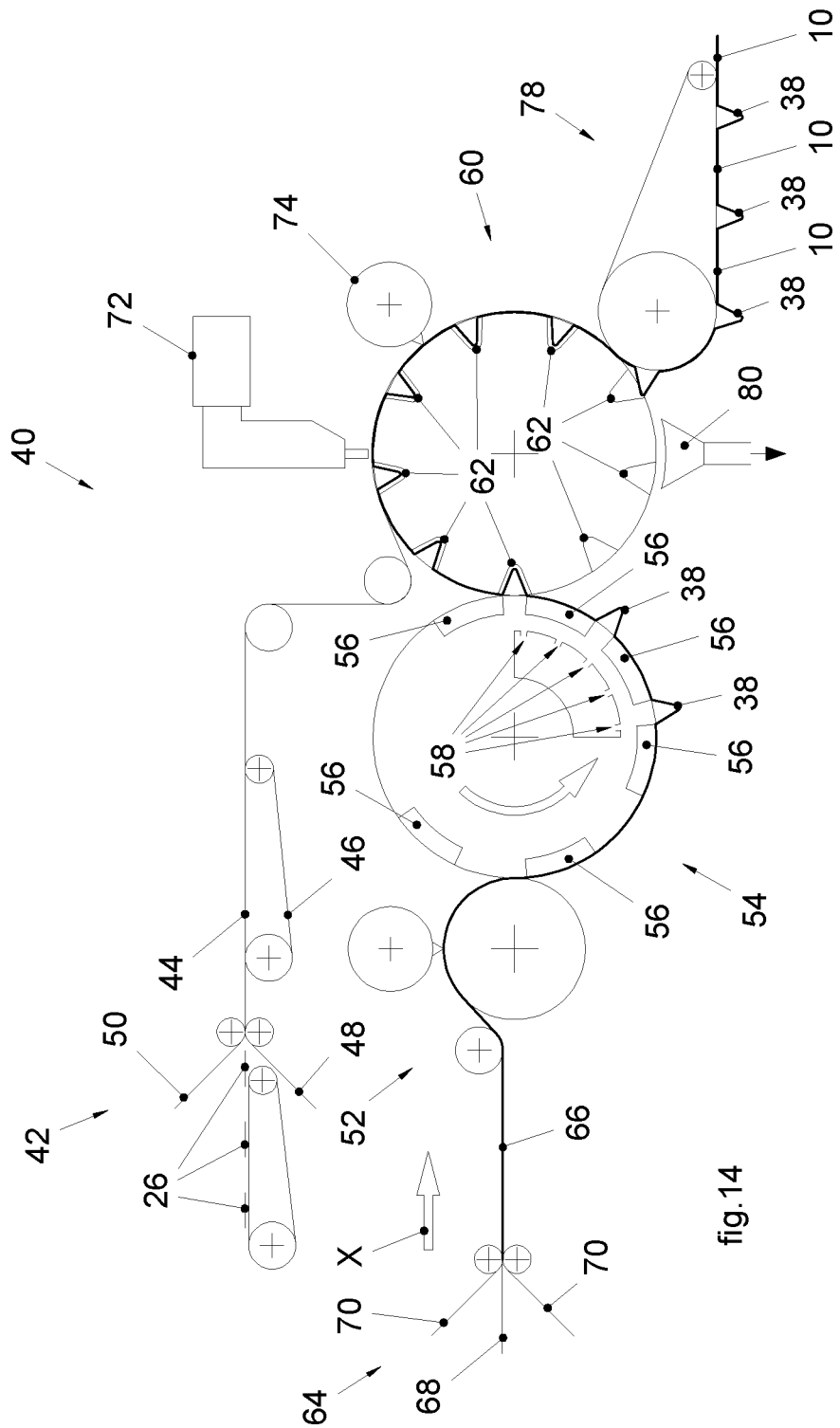
FIG. 14 is a schematic side view of an apparatus configured for producing the absorbent sanitary articles shown in FIGS. 3 and 4, and FIGS. 15-21 are schematic plan views showing various steps of a method for producing the absorbent sanitary articles shown in FIGS. 3 and 4.
Figure 15:
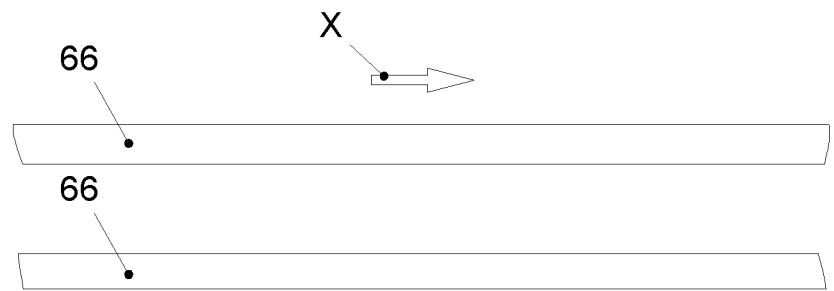
Figure 16:
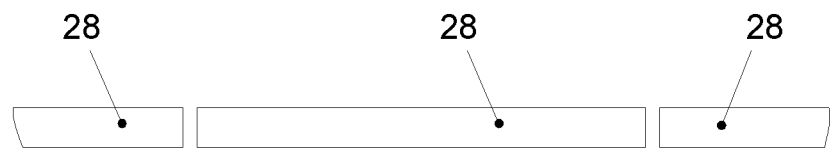

As compared to the embodiment described above, in the layout of the apparatus 40 the position of the first forming unit 42 and the second forming unit 64 change. The position of the other units and devices in the layout of the apparatus 40 remains as in the embodiment of FIG. 5. In the embodiment of FIG. 14, the second forming unit 64, configured to form the continuous elastic bands 66, is arranged upstream of the cutting device 52 and the repitching device 54 and the first forming unit 42, configured to form the continuous absorbent web 44, is arranged to feed the continuous absorbent web 44 to the anvil wheel 60 downstream of the repitching device 54.

The operation of the apparatus 40 shown in FIG. 14 is as follows.

Figure 17:
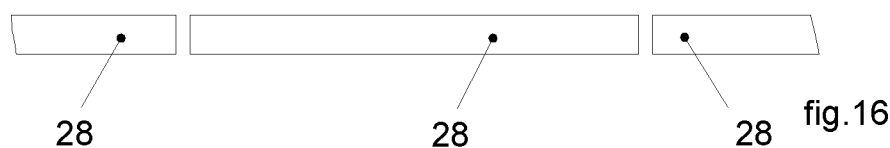
Figure 18:
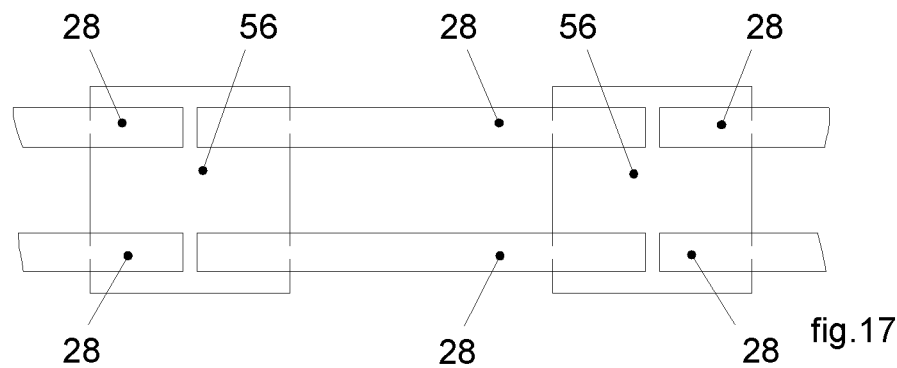

The second forming unit 64 forms two continuous elastic bands 66 (FIG. 15) which advance in the machine direction X towards the cutting device 52. The cutting device 52 transversely cuts the two continuous elastic bands 66, and forms pairs of elastic bands 28 (FIG. 16) with a predetermined length. The pairs of elastic bands 28 at the outlet of the cutting device 52 are picked up by the repitch device 54. Each pair of elastic bands 28 is picked up by two adjacent gripping elements 56 (FIG. 17). During the path from the pick-up station to the release station, the gripping elements 56 approach each other and form loops 38 on the pairs of elastic bands 28 (FIG. 18). The nozzles 58 emit jets of air between the gripping elements 56 in order to push outwards the loops 38 formed on the elastic bands 28.

The elastic bands 28 may be formed and transported to the repitching device 54 in the stretched state, or in a substantially relaxed state. In any case, loops 38 are formed when the gripping elements 56 approach each other.

If the elastic bands 28 are in a stretched state, to form the loops 38, the gripping elements 56 must approach each other by a distance such as to cancel the stretched state of the elastic bands and form the loops 38. It is not relevant whether the elastic bands are formed and processed in a stretched or relaxed state. What is relevant is that—in the repitch device 54—the elastic bands 28 are treated so as to form the loops 38.

At the outlet of the repitching device 54, the elastic bands 28 are transferred to the outer surface of the anvil wheel 60. The recesses 62 of the anvil wheel 60 receive respective loops 38 of the elastic bands 28.

Figure 19:
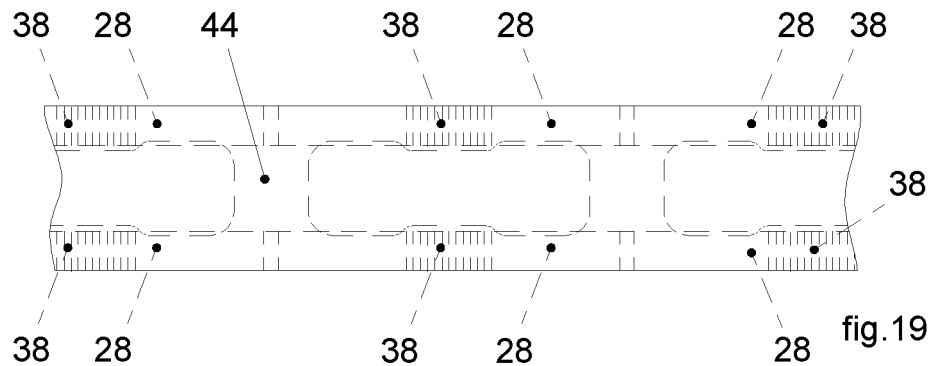

The first forming unit 44 feeds the continuous absorbent web 44 on the outer surface of the anvil wheel above the elastic bands 28 provided with loops 38 (FIG. 19).

Figure 20:
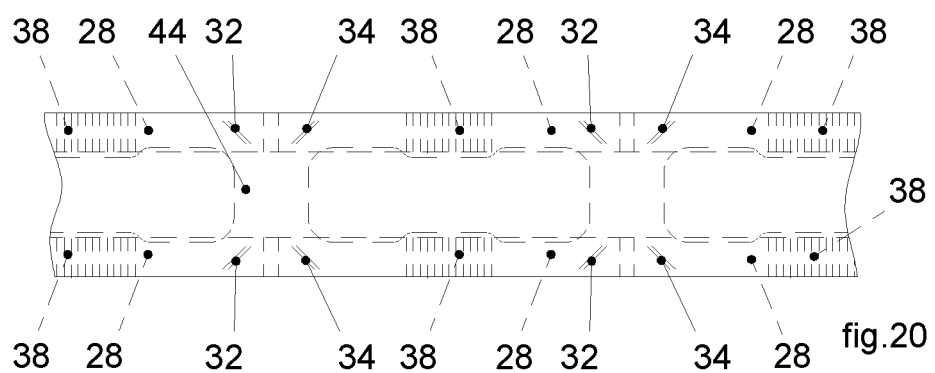

The ultrasonic welding device 72 welds the continuous absorbent web 44 to the elastic bands 28 along oblique welding lines 32, 34, having a V shape open outwards (FIG. 20).

Figure 21:
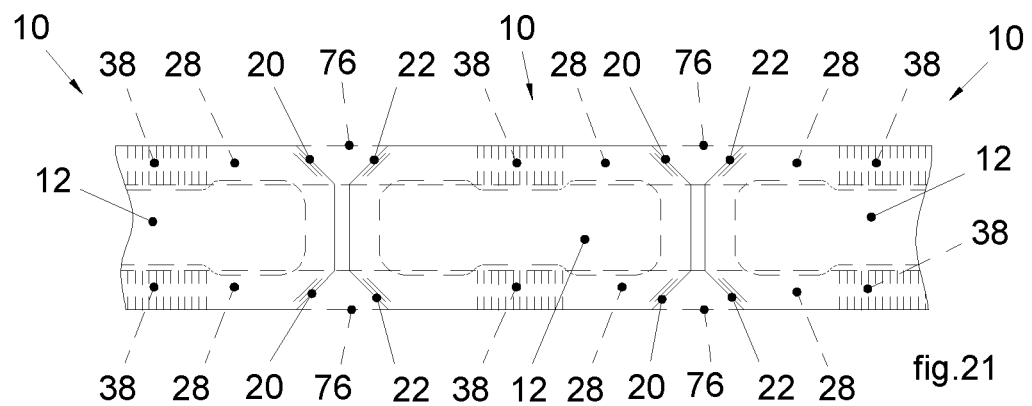

The cutting device 74 cuts the continuous absorbent web 44 and the elastic bands 28 along cutting lines having a double Y shape (FIG. 21). The oblique cutting lines originate the oblique sides 20, 22 and the front and rear transversal sides 16, 18 of the finished absorbent sanitary articles 10. The triangular-shaped portions 76 comprised between the oblique sides 20, 22, indicated by a dashed line in FIG. 21, constitute scraps.

The sections of the continuous absorbent sheet 44 comprised between the double Y-shaped cuts form the absorbent bodies 12 of the finished absorbent sanitary articles 10.

In a possible embodiment, the cutting device 52 and the repitching device 54 may be arranged both downstream of the first forming unit 44 and downstream of the second forming unit 64, so as to form loops 36, 38 both on the absorbent bodies 12 and on the elastic bands 28.

In a possible embodiment, the absorbent sanitary article 10 may comprise the loops 36, 38 formed on the absorbent body 12 and/or on the elastic bands 28 folded on the surface facing outwards respectively of the absorbent body and/or of the elastic bands. In a possible embodiment, the loops 36, 38 folded respectively on the outward-facing surface of the absorbent body 12 and/or of the elastic bands 28 may comprise temporary connecting points in order to be kept in this configuration to facilitate subsequent operations on the articles 10, for example, packaging.

In a possible embodiment, the method for producing absorbent sanitary articles 10 may comprise the step of folding the loops 36, 38 formed on the absorbent bodies 12 and/or the elastic bands 28, and possibly the step of fixing them in a folded configuration by means of temporary connecting points in respective temporary folding and fixing units.

In a packaged article folded in two, a loop on the absorbent body or on the elastic bands that is not actually folded back on itself may not be detectable. If the loop is formed on the absorbent body, in the extended configuration, the absorbent body is longer than the elastic bands at their maximum elastic extension. Similarly, if the loops are formed on the elastic bands, in an unstretched configuration the elastic bands are longer than the absorbent body.

Of course, without prejudice to the principle of the invention, the details of construction and the embodiments can be widely varied with respect to those described and shown, without thereby departing from the scope of the invention as defined by the claims that follow.

The invention claimed is:

1. A method for producing absorbent sanitary articles, comprising:
    forming absorbent bodies elongated along a longitudinal axis, and having respective longitudinal sides,
    forming elastic bands,
    coupling the elastic bands and the absorbent bodies to each other parallel to said longitudinal axis at the longitudinal sides of absorbent bodies, and
    fixing the elastic bands and the absorbent bodies together along two front and two rear inclined joint lines,
    wherein the method further comprises the step of forming transverse loops on said absorbent bodies and/or on said elastic bands before fixing the elastic bands and the absorbent bodies together, so as to form absorbent sanitary articles provided with elastic bands having a length in an extended condition that is different from a length in an extended condition of the respective absorbent bodies.

2. The method according to claim 1, comprising:
    forming a continuous absorbent web having a longitudinal axis,
    cutting the continuous absorbent web transversely so as to form absorbent bodies separated from each other,
    forming the transverse loops on respective absorbent bodies,
    forming two continuous elastic bands,
    fixing said two continuous elastic bands to the absorbent bodies provided with the transverse loops along the inclined joint lines, and
    cutting the continuous elastic bands and the absorbent bodies provided with the transverse loops along inclined cutting lines.

3. The method according to claim 1, comprising the step of transferring said absorbent bodies and/or said elastic bands provided with the transverse loops onto an anvil wheel provided with recesses that receive respective transverse loops.

4. A method for producing absorbent sanitary articles, comprising:
    forming absorbent bodies elongated along a longitudinal axis, and having respective longitudinal sides,
    forming elastic bands,
    coupling the elastic bands and the absorbent bodies to each other parallel to said longitudinal axis,
    fixing the elastic bands and the absorbent bodies together along inclined joint lines,
    forming transverse loops on said absorbent bodies and/or on said elastic bands before fixing the elastic bands and the absorbent bodies together, so as to form absorbent sanitary articles provided with elastic bands having a length in an extended condition that is different from a length in an extended condition of the respective absorbent bodies,
    forming two continuous elastic bands,
    transversely cutting the two continuous elastic bands so as to form pairs of elastic bands separated from each other,
    forming the transverse loops on respective pairs of elastic bands,
    forming a continuous absorbent web having a longitudinal axis,
    attaching the continuous absorbent web to said elastic bands provided with the transverse loops along the inclined joint lines, and
    cutting the continuous elastic bands and the absorbent bodies provided with the transverse loops along inclined cutting lines.

5. The method according to claim 4, comprising the steps of:
    picking up said elastic bands by gripping elements, and
    bringing said gripping elements closer to each other to form said transverse loops.

6. The method according to claim 5, comprising emitting jets of air between said gripping elements to push said transverse loops outwards.

7. A method for producing absorbent sanitary articles, comprising the steps of:
    forming absorbent bodies elongated along a longitudinal axis, and having respective longitudinal sides,
    forming elastic bands,
    coupling the elastic bands and the absorbent bodies to each other parallel to said longitudinal axis,
    fixing the elastic bands and the absorbent bodies together along inclined joint lines,
    forming transverse loops on said absorbent bodies and/or on said elastic bands before fixing the elastic bands and the absorbent bodies together, so as to form absorbent sanitary articles provided with elastic bands having a length in an extended condition that is different from a length in an extended condition of the respective absorbent bodies,
    forming a continuous absorbent web having a longitudinal axis,
    cutting the continuous absorbent web transversely so as to form the absorbent bodies separated from each other,
    forming the transverse loops on respective absorbent bodies,
    forming two continuous elastic bands,
    fixing said two continuous elastic bands to the absorbent bodies provided with the transverse loops along the inclined joint lines, and
    cutting the continuous elastic bands and the absorbent bodies provided with the transverse loops along inclined cutting lines,
    picking up said absorbent bodies by gripping elements, and
    bringing said gripping elements closer to each other to form said transverse loops.

8. The method according to claim 7, comprising emitting jets of air between said gripping elements to push said transverse loops outwards.

\* \* \* \* \*